United States Patent
Gurkaynak et al.

(10) Patent No.: US 6,849,764 B2
(45) Date of Patent: Feb. 1, 2005

(54) PRODUCTION OF POTASSIUM FORMATE

(75) Inventors: Mehmet Ali Gurkaynak, Bostanci-Istanbul (TR); Isa Uzun, Gemlik-Bursa (TR)

(73) Assignee: MKS Marmara Entegre Kimya San A.S. (TR)

( * ) Notice: Subject to any disclaimer, the term of this patent is extended or adjusted under 35 U.S.C. 154(b) by 0 days.

(21) Appl. No.: 10/331,426

(22) Filed: Dec. 30, 2002

(65) Prior Publication Data

US 2004/0127745 A1 Jul. 1, 2004

(51) Int. Cl.⁷ .............................................. C07C 53/06
(52) U.S. Cl. ..................................................... 562/609
(58) Field of Search ......................................... 562/609

(56) References Cited

U.S. PATENT DOCUMENTS 4,301,310 A * 11/1981 Wagner ....................... 568/863

FOREIGN PATENT DOCUMENTS

GB 366 556 A 2/1932
WO WO 96/01248 1/1996

* cited by examiner

Primary Examiner—Paul A. Zucker
(74) Attorney, Agent, or Firm—Duke W. Yee; Gerald H. Glanzman

(57) ABSTRACT

This invention relates to a process for the continuous production of potassium formate by the reaction of formaldehyde present in the reactor outlet gas in formaldehyde production plants with an aqueous solution of potassium hydroxide, wherein the formaldehyde is in gaseous monomeric form, the formaldehyde being fed to the reaction column at a temperature of 100° C. and above. By this invention, a straightforward method of potassium formate production and removal of excess reactant(s) are realized very efficiently. Pure potassium formate solution at any strength is produced. The strength of the product solution depends on where it will be used. Potassium Formate solution is used mainly as deicer, drilling mud, and/or in the production of flaked or granular Potassium Formate by appropriate methods. The flaked and granular Potassium Formate in turn is used in the fields mentioned above and also as an additive to animal feed.

14 Claims, No Drawings

PRODUCTION OF POTASSIUM FORMATE

BACKGROUND OF THE INVENTION

1. Technical Field

The present invention relates to an improved process for the continuous production of potassium formate by the reaction of gaseous monomeric formaldehyde with potassium hydroxide. Particularly, the invention relates to a straightforward method wherein potassium formate production and removal of excess reactant(s) is realized very efficiently from monomeric gaseous formaldehyde present in the reactor outlet gas in formaldehyde production plants.

2. Description of Related Art

Potassium formate solution is used mainly as deicer, drilling mud, and/or in the production of flaked or granular potassium formate by appropriate methods. The flaked and granular potassium formate inturn is used in the fields mentioned above as well as an additive to animal food.

There has been conventionally provided several methods for the production of potassium formate. One production method thereof is the reaction between formic acid and potassium hydroxide solution, but since formic acid is expensive this method is not economical. Another method is by reacting carbon monoxide and potassium hydroxide solution, which results in some drawbacks such as high reaction temperatures and pressures and low reaction rates. Still another method is the production of pentaerythritol where potassium formate is the byproduct when potassium hydroxide is used as the catalyst.

Furthermore, there was also provided several approaches in industrial scale, for example, wherein a reaction between formaldehyde solution and potassium hydroxide solution, substantially in liquid forms, is carried out for the production of potassium formate. The basic disadvantages thereof are high energy consumption for the evaporation of water coming with formaldehyde solution; not too fast reaction rate compared to the present invention; being a batch reaction; the storage and transportation problems of methanol obtained after the distillation of the product solution; and the difficulties in elimination and consumption of the large amount of water contaminated with methanol obtained during the purification of the product solution.

SUMMARY OF THE INVENTION

The present invention discloses an improved process for the continuous production of potassium formate (KHCOO) by the reaction of gaseous monomeric formaldehyde with potassium hydroxide in order to overcome the above mentioned drawbacks.

By this invention a straightforward method of Potassium Formate production and removal of excess reactant(s) are realized very efficiently. Pure Potassium Formate solution at any strength is produced. The strength of the product solution depends on where it will be used.

The reaction is carried at high pH values, predetermined temperatures and reactant concentrations in a specially designed and manufactured absorption-reaction column working at atmospheric pressure. The monomeric formaldehyde is in gaseous state at a temperature above 100° C. and the potassium hydroxide is in solution form in water at a concentration of 15 to 60% by weight.

The excess of the reactant(s) and methanol produced are removed and recovered by various physical and chemical operations. The methanol produced is immediately fed back to the formaldehyde reactor eliminating the needs for its storage and transportation. The small amount of water contaminated with methanol obtained during the purification operation of the product solution is immediately used in the preparation of potassium hydroxide solution from flaked potassium hydroxide.

The product potassium formate solution according to the invention is water clear neutral liquid without almost any contaminants. The product solution has potassium formate concentration between 40 to 80% by weight depending on where it will be used. Furthermore, the product solution is converted into granular or flaked form with potassium formate concentration of at least 97% by weight by using conventional concentration and drying operations.

DETAILED DESCRIPTION OF THE INVENTION

According to the invention, potassium formate solution and methanol are produced without almost any side products and impurities, by conducting the reaction at certain hydroxyl ion concentration, at certain temperature range, by choosing a removal method for one of the products, and by keeping the contact surface between gaseous monomeric formaldehyde and potassium hydroxide solution as high as possible and economically feasible, The reaction mechanism is as follows (aqueous):

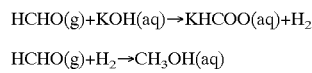

$$HCHO(g) + KOH(aq) \rightarrow KHCOO(aq) + H_2$$

$$HCHO(g) + H_2 \rightarrow CH_3OH(aq)$$

Overall reaction is (aqueous):

$$2HCHO(g) + KOH(aq) \rightarrow KHCOO(aq) + CH_3OH \quad (1)$$

In order to have high conversion rate and efficiency without any significant side reactions that will contaminate the product and lower the yield, it is found that the reaction must be carried in a certain well designed packed column, at certain temperature range, at certain pH range (hydroxyl ion concentration), and at certain reactant concentrations. Since the product concentration is mainly determined by the reactant concentrations its influences are the same with those of the reactant concentrations.

By "certain well designed packed column" herein is meant an absorption-reaction column with three stages, each stage being about 3000 mm high and filled with appropriate packings and liquid circulation pumps and lines. Also, above the packed sections there are 15 to 20 perforated trays in the column. Furthermore, there is another packed section about 3000–3500 mm high above the perforated tray section of the column in order to scrub the trace amount of methanol carried by the gas. This methanol scrubbing section also has a liquid circulation system with a plate heat exchanger to cool the liquid.

The reactor outlet gas coming from the formaldehyde reactor is fed to the bottom of the column above 100° C. in order to assure that formaldehyde is in pure monomeric state. The potassium hydroxide solution is fed to the column above the perforated trays and below the methanol scrubbing section. The trace amount of methanol is scrubbed with small amount of cold water and the accumulated methanol in water is withdrawn from the collector just below the methanol scrubbing section of the column. This methanol rich solution is mixed with the methanol solution in water obtained during the concentration operation of the main potassium formate solution in a separate section of the plant described in the coming sections of the present invention.

By "certain temperature range" herein is meant the temperature of the liquid circulating in the three packed stages of the column where reaction takes place to be from 20 to 100° C. The choice of the temperature is related to the potassium formate concentration of the product solution taken from the bottom of the column, the higher is the temperature the higher is the concentration, which means the lower is the cost of final treatment of the product solution. On the other hand at lower temperatures it is easier to control the reaction concerning the side reactions. In the present invention, it is found that the optimum temperature range is from 40 to 60° C.

By "certain pH range" herein is meant the hydroxyl ion concentration of the reaction solution that must be maintained all through the reaction and expressed as pH. The optimum pH is in between 11 to 14, and specifically from 12 to 13. At lower pH values the reaction rate decreases and the free formaldehyde content of the product solution increases. The increase in free formaldehyde content of the product solution causes discoloration of the final product solution during the concentration operation.

By "certain reactant concentrations" herein is meant the concentration of the potassium hydroxide solution fed to the reaction column above the perforated trays of the column. According to the present invention the concentration of potassium hydroxide solution fed to the reaction column is from 15 to 60% by weight, and more precisely it is from 30 to 45% by weight. The concentration of monomeric formaldehyde in the gas fed to the reaction column is from 6 to 9% by weight, and more precisely it is from 7 to 8% by weight.

According to the invention, the product solution accumulated in the bottom of the reaction column is continuously withdrawn to a separate neutralization tank where the excess potassium hydroxide in the product liquid is neutralized to a pH from 6 to 8, and more precisely from 6.5 to 7.5 with a suitable organic acid, preferably formic acid. The product liquid withdrawn from the bottom of the reaction column has potassium formate concentration of 20 to 50% by weight, more precisely 30 to 40% by weight.

According to the invention, the neutralized solution is continuously fed to a conventional multiple effect evaporation unit where the methanol in the solution is separated, and sent to the methanol recovery and enriching column. Furthermore, after separating the methanol from the solution, the water remaining in the product is removed in the second and third stages of the multiple effect evaporation system to such a degree that the product reaches the desired final potassium formate concentration. The potassium formate concentration of the final solution leaving the evaporation system is from 40 to 95% by weight depending on where it will be used. If the potassium formate will be used as a solution in water its concentration is from 40 to 75% by weight, it is cooled to room temperature and stored in 1 m³ polyethylene containers without crystal formation. If the potassium formate will be converted to granular or flaked form the concentration of the solution leaving the evaporation system is from 93 to 95% by weight, and it is granulated or flaked with conventional drying operations and bagged in air impermeable thick, and well sealed polyethylene bags.

According to the present invention the conversion based on the convertible formaldehyde is above 99% by weight.

What is claimed is:

1. A process for the continuous production of potassium formate by absorption and reaction of gaseous monomeric formaldehyde with an aqueous solution of potassium hydroxide in a column reactor equipped with packed sections and sieve trays, and operated under atmospheric pressure.

2. A process according to claim 1, wherein the gaseous monmeric formaldehyde is fed to the column reactor at a temperature of at least 100° C., and a temperature of a reaction solution circulating in the column reactor is from 20 to 100° C.

3. A process according to claim 1, wherein an aqueous potassium hydroxide solution is continuously fed to the column reactor at such a flow rate to keep pH of a reaction medium from 11 to 14.

4. A process according to claim 1, wherein the concentration of potassium hydroxide fed to the column reactor is from 15 to 60% by weight.

5. A process according to claim 1, wherein a product solution withdrawn from the bottom of the column reactor has a potassium formate concentration from 20 to 50% by weight.

6. A process according to claim 1, wherein a product solution continuously withdrawn from the bottom of the column reactor is neutralized to a pH from 6 to 8 with an organic acid.

7. A process according to claim 1, wherein methanol and part of water in a product solution is removed, and a final potassium formate solution with a concentration from 40 to 95% by weight is produced, the methanol removed being fed back to a formaldehyde reactor.

8. A process according to claim 1, wherein a 93–95% by weight potassium formate solution is used to produce flaked or granular potassium formate by a drying operation, and a potassium formate solution from 40 to 75% potassium formate by weight is stored and supplied in liquid form.

9. A process according to claim 2, wherein the temperature of the reaction solution circulating in the column reactor is from 40 to 60° C.

10. A process according to claim 3, wherein the pH of the reaction medium is kept from 12 to 13.

11. A process according to claim 4, wherein the concentration of potassium hydroxide fed to the column reactor is from 30 to 45% by weight.

12. A process according to claim 5, wherein the product solution withdrawn from the bottom of the column reactor has a potassium formate concentration from 30 to 40% by weight.

13. The process according to claim 6, wherein the product solution continuously withdrawn from the bottom of the column reactor is neutralized to a pH from 6.5 to 7.5.

14. The process according to claim 6, wherein the organic acid comprises formic acid.

* * * * *

UNITED STATES PATENT AND TRADEMARK OFFICE
CERTIFICATE OF CORRECTION

PATENT NO. : 6,849,764, B2
DATED : February 1, 2005
INVENTOR(S) : Gurkaynak et al.

It is certified that error appears in the above-identified patent and that said Letters Patent is hereby corrected as shown below:

Column 1,
Line 20, after "animal" delete "food" and insert -- feed --.

Signed and Sealed this

Third Day of January, 2006

JON W. DUDAS
*Director of the United States Patent and Trademark Office*